United States Patent
van Boeckel et al.

(10) Patent No.: US 6,174,863 B1
(45) Date of Patent: Jan. 16, 2001

(54) CARBOHYDRATE DERIVATIVES

(75) Inventors: Constant Adriaan Anton van Boeckel, Oss (NL); Maurice Petitou, Paris; Philippe Duchaussoy, Toulouse, both of (FR); Cornelia Maria Dreef-Tromp, Wijchen; Johannes Egbertus Maria Basten, Afferden, both of (NL)

(73) Assignee: Akzo Nobel N.V., Arnhem (NL)

( * ) Notice: Under 35 U.S.C. 154(b), the term of this patent shall be extended for 0 days.

(21) Appl. No.: 09/193,901

(22) Filed: Nov. 18, 1998

(30) Foreign Application Priority Data

Nov. 19, 1997 (EP) .................................................. 97203613

(51) Int. Cl.[7] ........................ A61K 31/70; A61K 31/727; C07H 11/00
(52) U.S. Cl. ................................ 514/25; 514/54; 514/56; 536/4.1; 536/18.2; 536/21; 536/118; 536/122; 536/123.1
(58) Field of Search .................................. 514/54, 25, 56; 536/21, 118, 122, 123.1, 4.1, 18.2

(56) References Cited

FOREIGN PATENT DOCUMENTS

| 0 300 099 | 1/1989 | (EP) . |
|---|---|---|
| 0 301 618 | 2/1989 | (EP) . |
| 0 454 220 | 10/1991 | (EP) . |
| 0 529 715 | 3/1993 | (EP) . |

OTHER PUBLICATIONS

Petitou et al. *J. Med. Chem.* 1997, 40, 1600–1607. (month not available).*

* cited by examiner

*Primary Examiner*—Kathleen K. Fonda
(74) *Attorney, Agent, or Firm*—William M. Blackstone

(57) ABSTRACT

The invention relates to a carbohydrate derivative having formula I

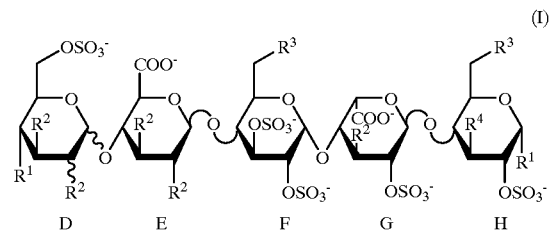

wherein $R^1$ is (1–4C)alkoxy; $R^2$, $R^3$ and $R^4$ are independently (1–4C)alkoxy or $OSO_3^-$, the total number of sulfate groups is 4, 5, or 6; and the twisted lines represent bonds either above or below the plane of the six-membered ring to which they are attached; or a pharmaceutically acceptable salt thereof.

The compounds of the invention have antithrombotic activity and may be used for treating or preventing thrombosis and for inhibiting smooth muscle cell proliferation.

9 Claims, No Drawings

CARBOHYDRATE DERIVATIVES

FIELD OF THE INVENTION

The invention relates to a carbohydrate derivative, a pharmaceutical composition containing the same, as well as the use of said carbohydrate derivative for the manufacture of a medicament.

BACKGROUND OF THE INVENTION

Heparin is a commonly used anticoagulant from biological sources such as intestinal mucosa. In the presence of heparin, the inactivation of thrombin by anti-thrombin III (AT-III) is greatly accelerated, involving changes in both the conformation of heparin and AT-III on complexation. Thrombin regulates the last step in the blood coagulation cascade. The prime function of thrombin is the cleavage of fibrinogen to generate fibrin monomers, which form an insoluble gel, a fibrin clot, by cross-linking.

The structural features of heparin that are required for interacting AT-III have been subject to various investigations. There are parts in the heparin polymer which show only low affinity for AT-III, whereas other parts were found to be more important for binding to AT-III. Studies of fragmented heparin have finally resulted in the identification of a pentasaccharide fragment accounting for the minimal high-affinity structure that binds to AT-III (see e.g. Physiological Reviews, 71 (2), 488/9, 1991). In this high-affinity fragment eight sulfate groups are present. Four of the sulfate groups were found to be essential for binding to AT-III (Advances in Carbohydrate Chemistry and Biochemistry; Vol. 43; Eds. R. S. Tipson, D. Horton; Publ. Harcourt Brace Jovanovich; B. Casu (pages 51–127), paragraph 6), whereas the other further attribute to higher affinity. This finding was confirmed in synthetic analogues of the pentasaccharide fragment (see e.g. Agnew. Chem. 32 (12), 1671–1818, 1993).

The identification of the high-affinity pentasaccharide fragment inspired the preparation of synthetic analogues thereof. Small synthetic carbohydrate molecules of the glycosaminoglycan type were found to be potent and selective anti-Xa inhibitors. See for instance European patent 84,999. Later filed patents/patent applications showed that many variants of these molecules have similar and even higher activities and further improved pharmacological properties, such as the glycosaminoglycan-related carbohydrate derivatives disclosed in EP 529,715 and EP 454,220. These carbohydrate derivatives are devoid of the characteristic functional groups of glycosaminoglycans: free hydroxyl groups, N-sulfate and N-acetyl groups. Further, all of the pentasaccharides disclosed in these latter patent applications carry at least seven sulfate groups. In the field of antithrombotic oligosaccharide derivatives it was thus generally assumed that at least seven sulfate groups are required in pentasaccharide compounds in order to obtain clinically acceptable levels of antithrombotic activity.

Unexpectedly, however, a class of glycosaminoglycan-related carbohydrate derivatives has now been found having only four to six sulfate groups and which still display significant clinically effective antithrombotic activity. In addition, the compounds of this invention show fewer side effects. For example, bleeding risks are reduced and the low sulfate content of the compounds does not give rise to heparin-induced thrombocytopenia (HIT) [HIT is a severe side effect, which may be the cause of the death of a patient]. Further, compounds of this invention have a biological half-life which allows once-a-day-treatment. Once-a-day-treatment may be considered to be more favourable than, for example, once-a-week-treatment, allowing quick adaptation of the medical treatment is the condition of a patient requires so. Also hospital logistics are easier with one-a-day-treatment, as no complex dosing schemes are required for the treatment of the patients.

Thus, the compounds of the invention display an unexpected and delicately balanced pharmacological profiles.

SUMMARY OF THE INVENTION

The invention therefore relates to a carbohydrate derivative having formula I

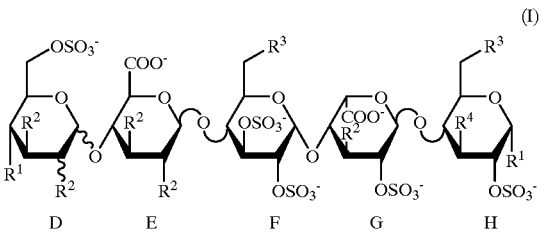

wherein $R^1$ is (1–4C)alkoxy; $R^2$, $R^3$ and $R^4$ are independently (1–4C)alkoxy or $OSO_3^-$; the total number of sulfate groups is 4, 5 or 6; and the twisted lines represent bonds either above or below the plane of the six-membered ring to which they are attached; or a pharmaceutically acceptable salt thereof.

The compounds of the present invention are useful for treating and preventing thrombin-mediated and thrombin-associated diseases. This includes a number of thrombotic and prothrombotic states in which the coagulation cascade is activated which include, but are not limited to, deep vein thrombosis, pulmonary embolism, thrombophlebitis, arterial occlusion from thrombosis or embolism, arterial reocclusion during or after angioplasty or thrombolysis, restenosis following arterial injury or invasive cardiological procedures, postoperative venous thrombosis or embolism, acute or chronic atherosclerosis, stroke, myocardial infarction, cancer and metastasis, and neurodegenerative diseases. The carbohydrate derivatives of the invention may also be used as inhibitors of smooth muscle cell proliferation and for the treatment of angiogenesis, cancer and retrovirus infections, like HIV.

Further, the compounds of the invention may be used as anticoagulants and anticoagulant coatings in extracorporeal blood circuits, as necessary in dialysis and surgery.

The compounds of the invention may also be used as in vitro or ex vivo anticoagulants.

DETAILED DESCRIPTION OF THE INVENTION

Preferred carbohydrate derivatives according to the invention have the D-unit has the structure

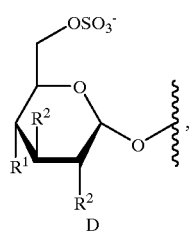

$R^1$ is methoxy; and $R^2$, $R^3$ and $R^4$ are independently methoxy or $OSO_3^-$.

More preferred carbohydrate derivatives are those wherein $R^2$ is methoxy. In particularly preferred carbohydrate derivatives $R^3$ is methoxy. The most preferred carbohydrate derivative is the one wherein $R^4$ is methoxy.

In the term (1–4C)alkoxy the (1–4C)alkyl group is a branched or unbranched alkyl group having 1 to 4 carbon atoms, such as methyl, ethyl, isopropyl, t-butyl, and the like. The most preferred alkyl group is methyl.

The counter-ions which compensate the charged moieties are pharmaceutically acceptable counter-ions, like hydrogen, or more preferably alkali or earth-alkali metal ions, like sodium, calcium, or magnesium.

The carbohydrate derivatives according to this invention may be prepared according to well known methods described and used for the synthesis of oligosaccharides. In this respect, in particular reference is made to the previously mentioned European patent EP 529,715. A suitable process for the preparation of the carbohydrate derivatives of formula I is characterized by a process wherein protected monosaccharides having different structures are coupled to give protected disaccharides, after which:

(a) protected disaccharides of one type are coupled to protected disaccharides of another type to give protected tetrasaccharides, which tetrasaccharides are coupled to a protected monosaccharide to give protected pentasaccharides; or (b) protected monosaccharides are coupled to protected disaccharides to give protected trisaccharides, which are further coupled to protected disaccharides to give protected pentasaccharides;

after which the protective groups are cleaved and free hydroxy groups are sulfated, after which the compound obtained is optionally converted into a pharmaceutically acceptable salt.

The monosaccharides are D-glucose, D-mannose, L-idose, D-glucuronic acid or L-iduronic acid, suitably functionalized with the required alkyl groups or by temporarily protective groups. Suitable protective groups are well known in the art. Preferred protective groups include benzyl and acetyl for hydroxy groups, and benzyl for the carboxylate groups of uronic acids. Other protective groups, such as benzoyl, levulinyl, alkoxyphenyl, chloroacetyl, trityl, and the like may be used with equal success. Coupling of the saccharide is performed in a manner known in the art, e.g. deprotection of the 1-position of the glycosyl-donor, and/or activation of this position (e.g. by making a bromide, pentenyl, fluoride, thioglycoside, or trichloroacetimide derivative) and coupling the activated glycosyl-donor with an optionally protected glycosyl-acceptor.

For the treatment of venous thrombosis or for the inhibition of smooth muscle cell proliferation the compounds of the invention may be administered enterally or parenterally, and for humans preferably in a daily dosage of 0.001–10 mg per kg body weight. Mixed with pharmaceutically suitable auxiliaries, e.g. as described in the standard reference, Gennaro et al., Remington's Pharmaceutical Sciences (18th ed., Mack Publishing Company, 1990, see especially Part 8: Pharmaceutical Preparations and Their Manufacture), the compounds may be compressed into solid dosage units, such as pills, tablets, or be processed into capsules or suppositories. By means of pharmaceutically suitable liquids the compounds can also be applied as an injection preparation in the form of a solution, suspension, emulsion, or as a spray, e.g. a nasal spray.

For making dosage units, e.g. tablets, the use of conventional additives such as fillers, colorants, polymeric binders and the like is contemplated. In general any pharmaceutically acceptable additive which does not interfere with the function of the active compounds can be used. Suitable carriers with which the compositions can be administered include lactose, starch, cellulose derivatives and the like, or mixtures thereof, used in suitable amounts.

The invention is further illustrated by the following examples.

EXAMPLES

Preparation of Example I (Compound 32)

Synthesis of GH Disachharide 16 (Scheme 1+2)

Compound 2

Compound 1 (60 g; commercially available) was dissolved in N,N-dimethylformamide (858 ml) together with benzyl bromide (50.5 ml). After cooling to +10° C. a 20% aqueous solution of sodium hydroxide was added dropwise. After stirring for 1 hour the temperature was raised to 20° C. and the mixture was stirred another 20 hours. The solution was then poured into a mixture of icewater and toluene and extracted. The organic layer was concentrated and the crude product purified by cristallysation to give 30.0 g of compound 2.

TLC: Rf=0.60, toluene/ethyl acetate: 7/3, v/v

Compound 3

Compound 2 (26.4 g) was dissolved in N,N-dimethylformamide (211 ml) and cooled in ice. Sodium hydride (2.5 g) was added under nitrogen atmosphere. Then 4-methoxy benzyl chloride (13.3 g) was added dropwise and the mixture was stirred for 1 hour at room temperature. The mixture was then diluted with ethyl acetate, washed with water (2x) and concentrated to give 40.7 g of crude compound 3.

TLC: Rf=0.80, toluene/ethyl acetate: 7/3, v/v

Compound 4

Compound 3 (34.9 g) was dissolved in 60% aq. acetic acid and stirred for 4 hours at 60° C. The mixture was diluted with toluene and concentrated. Purification by silicagel chromatography gave 26.4 g of compound 4.

TLC: Rf=0.07, toluene/ethyl acetate: 7/3, v/v

Compound 5

Compound 4 (26.4 g) was dissolved in dichloromethane (263 ml) under nitrogen atmosphere. Trimethyloxonium tetrafluoroborate (11.6 g) and 2,6-di-t-butyl-4-methylpyridine (17.4 g) were added at room temperature. After 4 hours the mixture was poured into ice-water and extracted with dichloromethane. The organic layer was washed with sodium hydrogencarbonate and evaporated. Purification of the crude product by silicagel chromatography gave 18.5 g of compound 5.

TLC: Rf=0.25, toluene/ethyl acetate: 7/3, v/v

Compound 7

Compound 6 (3-methyl-1,2,4,6-tetraacetyl-idose) (48.4 g) was dissolved in toluene (175 ml). Under nitrogen atmosphere ethanethiol (20 ml) and boron trifluoride diethyl etherate (1M in toluene; 134 ml) were added. After stirring for 1 hour aqueous sodium hydrogencarbonate (400 ml) was added and the mixture was stirred for another hour. The mixture was then poured into ethyl acetate. The organic layer was washed twice with water and concentrated. Purification by silicagel chromatography gave 29.6 g of compound 7.

TLC: Rf=0.45, toluene/ethyl acetate: 6/4, v/v

Compound 8

Compound 5 (17.5 g) and compound 7 (28.2 g) were dissolved in toluene (525 ml) under nitrogen atmosphere. After addition of powdered molsieves (4 Å) the reaction was cooled to −20° C. A freshly prepared 0.1 M solution of N-iodosuccinimide (17.4 g) and trifluoromethanesulphonic acid (1.38 ml) in dioxane/dichloromethane (1/1 v/v) were added dropwise under continuous nitrogen flux. After 10 minutes the red reaction mixture was filtered and washed successively with aqueous sodium thiosulphate and aqueous sodium hydrogencarbonate. The organic layer was concentrated in vacuo and 30.0 g of compound 8 isolated.

TLC: Rf=0.45, dichloromethane/ethyl acetate: 8/3, v/v

Compound 9

Compound 8 (30.0 g) was dissolved in 460 ml methanol/dioxane (1/1, v/v) and potassium butanolate was added for saponification. After 15 minutes the mixture was neutralised with Dowex 50WX8H$^+$-form and concentrated in vacuo. Purification was established by silicagel chromatography to give 17.4 g of compound 9.

TLC: Rf=0.25, dichloromethane/methanol: 95/5, v/v

Compound 10

Under nitrogen atmosphere compound 9 (17.4 g) was dissolved in N,N-dimethyl-formamide (77 ml). 1,2-dimethoxypropane (26 ml) and p-toluenesulfphonic acid where added and the mixture was stirred for 30 minutes. Diluting the mixture with aqueous sodium hydrogencarbonate and extracting it with ethyl acetate gave 19.7 of compound 10 after evaporation of the solvent.

TLC: Rf=0.45, dichloromethane/methanol: 95/5, v/v

Compound 11

Compound 10 (18.5 g) was dissolved in N,N,-dimethylformamide (24.4 ml) and cooled to 0° C. Under nitrogen atmosphere sodium hydride (1.47 g; 60% dispersion in oil) and iodomethane (2.36 ml) where added. After 1 hour excess of sodium hydride was neutralised, the mixture extracted with dichloromethane and concentrated to give 20.0 g of compound 11.

TLC: Rf=0.85, dichloromethane/methanol: 95/5, v/v

Compound 12

Compound 11 (18.4 g) was dissolved in dichloromethane (838 ml) and water (168 ml). 2,3-Dichloro-5,6-dicyano-1,4-benzoquinone (7.1 g) was added and the mixture was stirred for 18 hours at 4° C. The mixture was poured into aqueous sodium hydrogencarbonate and extracted with dichloromethane. Concentration of the organic layer gave 12.7 g of compound 12.

TLC: Rf=0.40, dichloromethane/methanol: 95/5, v/v

Compound 13

Compound 12 was converted to the title compound according to the same procedures described for the preparation of compound 11.

TLC: Rf=0.48, toluene/ethyl acetate: 1/1, v/v

Compound 14

After dissolving compound 13 (2.5 g) in acetic acid (14.6 ml) and water (6.1 ml) the mixture was stirred overnight at roomtemperature. Coevaporation with toluene and purification by silicagel chromatography gave 1.9 g of compound 14.

TLC: Rf=0.31, ethyl acetate, v/v

Compound 15

To a solution of compound 14 (1.7 g) in dichloromethane (9 ml) were added 2,2,6,6-tetramethyl-1-piperidinyloxy (5 mg), saturated sodium hydrogen carbonate solution (5.8 ml), potassium bromide (32 mg) and tetrabutylammonium chloride (42 mg). The mixture was cooled to 0° C. and a mixture of saturated sodium chloride solution (6.5 ml) saturated sodium hydrogen carbonate solution (3.2 ml) and sodium hypochlorite (1.3 M; 7.3 ml) was added during 15 minutes. After 1 hour stirring the mixture was diluted with water and extracted (3 times) with dichloromethane. The organic layer was washed with brine, dried on magnesium sulfate, filtered and evaporated to dryness to give 1.74 g of crude compound 15.

TLC: Rf=0.14, dichloromethane/methanol: 9/1, v/v

Methyl O-(benzyl 2,3-Di-O-methyl-α-L-idopyranosyluronate)-(1→4)-2-O-benzyl-3,6-Di-O-methyl-α-D-glucopyranoside 16

To a solution of 1.74 g of compound 15 in N,N-dimethylformamide was added under nitrogen atmosphere 1.68 ml of benzylbromide and 1.1 g of potassium hydrogen carbonate. After stirring the solution for 90 minutes water was added and the mixture extracted with ethyl acetate. After evaporation of the organic layer and purification by silicagel chromatography 1.64 g of compound 16 was isolated.

TLC: Rf=0.50, toluene/ethyl acetate: 1/1, v/v

Synthesis of EF-disaccharide 25 (Scheme 2+3)

Compound 17

Compound 12 (10.5 g) was dissolved in dry N,N-dimethylformamide (178 ml), cooled to 0° C. under nitrogen atmosphere. Sodium hydride (1.91 g; 60% dispersion in oil) was added after which benzylbromide (3.3 ml) was added dropwise. After 30 minutes the reaction was complete and the excess sodium hydride was neutralised. Water was added and the mixture extracted twice with ethyl acetate. Evaporation of the solvent gave 13.6 g of compound 17.

TLC: Rf=0.50, toluene/ethyl acetate: 1/1, v/v

Compound 18

Compound 17 was converted to the title compound according the same procedures described for the preparation of compound 14.

TLC: Rf=0.68, dichloromethane/methanol: 9/1, v/v

Compound 19

Compound 18 was converted to the title compound according the same procedures described for the preparation of compound 15.

TLC: Rf=0.14, dichloromethane/methanol: 9/1, v/v

Compound 20

Compound 19 was converted to the title compound according the same procedures described for the preparation of compound 16.

TLC: Rf=0.38, dichloromethane/methanol: 85/15, v/v

Compound 21

Compound 20 (9.9 g) was dissolved in 300 ml methanol (dry) and refluxed under nitrogen atmosphere. A 1 M solution of sodium methoxide (65.2 ml) was added dropwise and stirred for 3 hours. The temperature was then cooled to room temperature and 1N sodium hydroxide (22.2 ml) was added and stirred for 90 minutes. Neutralisation with Dowex 50WX8H$^+$ form and evaporation of the solvents gave the crude residue.

N,N-dimethylformamide (192 ml) and powdered molsieves (4 Å) were added under nitrogen atmosphere. Potassium hydrogencarbonate (3.2 g) and benzylbromide (4.8 ml) were added and the mixture stirred for 5 hours after which ethyl acetate was added and the mixture washed with water. Evaporation of the solvent and purification of the rude product by silicagel chromatography gave 6.19 g of compound 21 and 1.88 g of recovered compound 20.

TLC: Rf=0.74, dichloromethane/methanol: 9/1, v/v

Compound 22

Compound 21 (6.2 g) was dissolved in 40 ml of dioxane. Levulinic acid (2.1 g), dicyclohexyl carbodiimide (3.75 g) and 4-dimethylaminopyridine (0.2 g) where added and the mixture stirred for 2 hours under nitrogen atmosphere. Ether (95 ml) was added and the precipitate filtered off. The organic layer was washed with aqueous potassium hydrogensulphate and concentrated. Cristallisation from diethyl ether/heptane gave 6.2 g of compound 22.

TLC: Rf=0.26, dichloromethane/acetone: 95/5, v/v

Compound 23

Compound 22 (6.1 g) was dissolved in acetic anhydride (256 ml) under nitrogen atmosphere and cooled to −20° C. A mixture of sulphuric acid (4.9 ml) in acetic anhydride (49 ml) was added dropwise during 30 minutes. After 60 minutes sodium acetate was added until the pH of the mixture was neutral. Ethyl acetate and water where added and the organic layer concentrated. Purification by silicagel chromatography gave 4.2 g of compound 23.

TLC: Rf=0.63, dichloromethane/acetone: 9/1, v/v

Compound 24

Compound 23 (4.2 g) was dissolved in tetrahydrofuran (42 ml) and piperidine (4.1 ml) was added. The mixture was stirred overnight at room temperature. Ethyl acetate was added and the mixture washed with 0.5 N hydrochloric acid. The organic layer was concentrated and the residue purified by silicagel chromatography to give 3.2 g of compound 24.

TLC: Rf=0.33, dichloromethane/ethyl acetate: 1/1, v/v

O-(benzyl 2,3-di-O-methyl-4-O-levulinoyl-β-D-glucopyranosyluronate)-(1→4)-3-O-acetyl-2-O-benzyl-6-O-methyl-D-glucopyranosyl Trichloroacetimidate 25

Compound 24 (1.59 g) was dissolved in dichloromethane under nitrogen atmosphere. Trichloroacetonitril (1.1 ml) and cesium carbonate (72 mg) were added and the mixture stirred for 1 hour. The cesium carbonate was filtered off and the filtrate concentrated. Purification by silicagel chromatography gave 1.57 of compound 25.

TLC: Rf=0.60, toluene/ethyl acetate: 3/7, v/v

Synthesis of EFGH-tetrasaccharide 27 (Scheme 4)

Compound 26

A mixture of compound 16 (0.530 mg) and compound 25 (0.598 mg) was dried by coevaporation with dry toluene and dissolved in 8.2 ml of dry dichloromethane. Powdered molsieves (4 Å) was added and the mixture was cooled to −20° C. under nitrogen atmosphere and stirred for 30 minutes. To the resulting suspension was added trimethyl-silyl trifluoromethanesulphonate (15 mol % in relation to compound 25). After stirring for 10 minutes sodium hydrogencarbonate was added, the mixture was filtered and water and dichloromethane were added. The organic layer was then extracted, concentrated and the crude product purified by silicagel chromatography to give 0.62 g of compound 26.

TLC: Rf=0.47, toluene/ethyl acetate: 3/7, v/v

Methyl-O-(Benzyl 2,4-di-O-dimethyl-β-D-glucopyranosyluronate)-(1→4)-O-(3-O-acetyl-2-O-benzyl-6-O-methyl-α-D-glucopyranosyl)-(1→4)-O-(benzyl 2,3-di-O-methyl-α-L-idopyranosyluronate)-(1→4)-2-O-benzyl-3,6-di-O-methyl-α-D-glucopyranoside 27

To a solution of compound 26 (0.58 g) in pyridine was added a mixture of 2.76 ml acetic acid, 0.32 ml hydrazine hydrate in 2.1 ml pyridine. After 9 minutes, water and dichloromethane where added and the organic layer washed with 1 N hydrochloric acid and aqueous sodium hydrogencarbonate. Purification by silicagel chromatography gave 0.27 g of compound 27.

TLC: Rf=0.45, toluene/ethyl acetate: 3/7, v/v

Synthesis of DEFGH-pentasaccharide 32 (Scheme 4+5) Example I

Compound 29

A mixture of compound 27 (150 mg) and 76 mg of compound 28 (Ref: Bioorganic & Medicinal Chemistry, vol 2, no 11, 1267–1280, 1994) was dried by coevaporation with dry toluene and dissolved in 7.5 ml of dry dichloromethane. Under nitrogen atmosphere powdered molsieves (4 Å) was added and the mixture cooled to −20° C. After stirring for 20 minutes trimethylsilyl trifluoromethanesulphonate (15 mol % in relation to compound 28) was added. After stirring for 30 minutes aqueous sodium hydrogen-carbonate was added. The mixture was filtered and the organic layer was washed with water. Concentration of the solvent gave the crude product which was purified by silicagel chromatography to give 136 mg of compound 29.

TLC: Rf=0.33, toluene/ethyl acetate: 4/6, v/v

Compound 30

Compound 29 was diluted in a mixture of t-butanol (8 ml) and water (1 ml). To the solution 122 mg of 10% palladium on charcoal was added and the mixture was stirred overnight under hydrogen atmosphere. The palladium on charcoal was filtered and the solution was concentrated to give 84.5 mg of compound 30.

TLC: Rf=0.49, ethyl acetate/pyridine/acetic acid/water: 13/7/1.6/4, v/v

Compound 31 le;.5qCompound 30 (84.5 mg) was dissolved in 5 ml of 0.3 N sodium hydroxide and stirred and stirred for 3 hours. The reaction mixture was then neutralised with 0.5 N hydrochloric acid and evaporated. The residu was desalted on a Sephadex G25 column with water/acetonitril: 9/1 (v/v) and passed through a short column of Dowex 50WX8H$^+$-form. After evaporation 75.6 mg of compound 31 was isolated.

TLC: Rf=0.43, ethyl acetate/pyridine/acetic acid/water: 8/7/1.6/4, v/v

Methyl O-(2,3,4-tri-O-methyl-6-O-sulfo-α-D-glucopyranosyl)-(1→4)-O-(2,3-di-O-methyl-β-D-glucopyranosyluronic acid)-(1→4)-O-(6-O-methyl 2,3-di-O-sulfo-α-D-glucopyranosyl)-(1→4)-O-(2,3-di-O-methyl-α-L-idopyranosyluronic acid)-(1→4)-3,6-di-O-methyl-2-O-sulfo-α-D-glucopyranoside, Hexasodium Salt 32

Compound 31 (30.6 mg) was dissolved in 2.15 ml N,N-dimethylformamide (destilled; dry) and triethylamine sulfurtrioxide complex (120 mg) was added under nitrogen atmosphere. The mixture was stirred overnight at 55° C. A suspension of sodium hydrogencarbonate in water was added. The mixture was stirred for 1 hour at room temperature and the solvent evaporated. The residu was dissolved in water (2 ml) and desalted on a Sephadex G25-column with water/acetonitril: 9/1 (v/v). The isolated product was eluted on a Dowex 50WX8Na$^+$-column with water to give the 42.5 mg of pentasaccharide compound 32.

$[\alpha]^{20}_D$=+56.8 (c=1, H$_2$O)

Anomeric protons chemical shifts: 5.32, 5.22, 4.97, 4.89 and 4.24 ppm.

Preparation of Example II (Compound 38)

Synthesis of EFGH-tetrasaccharide 34 (Scheme 4)

Compound 33

Compound 25 and compound 20 were coupled to give the title compound according the same procedures described for the preparation of compound 26.

TLC: Rf=0.47, toluene/ethyl acetate: 3/7, v/v

Methyl-O-(Benzyl 2,4-di-O-dimethyl-β-D-glucopyranosyluronate)-(1→4)-O-(3-O-acetyl-2-O-benzyl-6-O-methyl-α-D-glucopyranosyl)-(1→4)-O-(benzyl 2,3-di-O-methyl-α-L-idopyranosyluronate)-(1→4)-2,3-di-O-benzyl-6-O-methyl-α-D-glucopyranoside 34

Compound 33 was converted to the title compound according the same procedures described for the preparation of compound 27.

TLC: Rf=0.39, heptane/ethyl acetate: 3/7, v/v

Synthesis of DEFGH-pentasaccharide 38 (Scheme 4+5) (Example II)

Compound 35

Compound 34 and compound 28 were coupled to give the title compound according the same procedures described for the preparation of compound 29.

TLC: Rf=0.60, toluene/ethyl acetate: 3/7, v/v

Compound 36

Compound 35 was converted to the title compound according the same procedure described for the preparation of compound 30.

TLC: Rf=0.39, ethyl acetate/pyridine/acetic acid/water: 13/7/1.6/4, v/v

Compound 37

Compound 36 was converted to the title compound according the same procedures described for the preparation of compound 31.

TLC: Rf=0.32, ethyl acetate/pyridine/acetic acid/water: 13/7/1.6/4, v/v

Methyl O-(2,3,4-tri-O-methyl-6-O-sulfo-α-D-glucopyranosyl)-(1→4)-O-(2,3-di-O-methyl-β-D-glucopyranosyluronic acid)-(1→4)-O-(6-O-methyl-2,3-di-O-sulfo-α-D-glucopyranosyl)-(1→4)-O-(2,3-di-O-methyl-α-L-idopyranosyluronic acid)-(1→4)-6-O-methyl-2,3-di-O-sulfo-α-D-glucopyranoside, Heptasodium Salt 38

Compound 37 was converted to the title compound according the procedures described for the preparation of compound 32.

$[\alpha]^{20}_D$=+53.6 (c=1, H$_2$O)

Anomeric protons chemical shift: 5.32, 5.23, 4.99, 4.9 and 4.23 ppm.

Preparation of Example III (Compound 56)

Synthesis of GH-disaccharide 50 (Scheme 1+2)

Compound 39

Compound 2 was converted to the title compound according the same procedures described for the preparation of compound 11.

TLC: Rf=0.52, dichloromethane/acetone: 98/2 v/v

Compound 40

Compound 39 (32.0 g) was dissolved in methanol (538 ml). p-Toluenesulfonic acid (1.57 g) was added and the mixture was stirred for 1.5 hour at room temperature. After neutralization with triethylamine the mixture was concentrated. Purification by silicagel chromatography gave 11.9 g of compound 40.

TLC: Rf=0.56, dichloromethane/methanol: 9/1, v/v

Compound 41

Compound 40 was converted to the title compound according the same procedures described for the preparation of compound 5.

TLC: Rf=0.18, toluene/ethyl acetate: 7/3, v/v

Compound 42

Compound 6 was converted to the title compound according the same procedure described for compound 24.

Compound 43

Compound 42 was converted to the title compound according the same procedures described for the preparation of compound 25.

Compound 44

The coupling reaction of compound 43 with compound 41 was performed under the same conditions as described for compound 26.

TLC: Rf=0.28, toluene/ethyl acetate: 6/4, v/v

Compound 45

Compound 44 was converted to the title compound according the same procedures described for the preparation of compound 9.

TLC: Rf=0.09, toluene/ethyl acetate: 3/7, v/v

Compound 46

Compound 45 was converted to the title compound according the same procedures described for the preparation of compound 10.

TLC: Rf=0.52, ethyl acetate

Compound 47

Compound 46 (10.4 g) was dissolved in pyridine (dry) (102 ml) under nitrogen atmosphere. A mixture of acetic anhydride (34 ml) and pyridine (dry) (102 ml) and 10 mg of 4-dimethylaminopyridine was added. After stirring for 1 hour at room temperature the reaction mixture was concentrated and coevaporated with dry toluene to give 11.9 g of compound 47.

TLC: Rf=0.50, toluene/ethyl acetate: 1/1, v/v

Compound 48

After dissolving compound 47 (11.9 g) in methanol (90 ml), 180 mg of p-toluenesulphonic acid was added and the mixture was stirred overnight at room temperature. The mixture was diluted with ethyl acetate, washed with water (2×) and concentrated. Purification of the crude product by silicagel chromatography gave 6.2 g of compound 48.

TLC: Rf=0.28, toluene/ethyl acetate: 3/7, v/v

Compound 49

Compound 48 was converted to the title compound according the same procedures described for the preparation of compound 15.

TLC: Rf=0.24, dichloromethane/methanol: 9/1, v/v

Methyl O-(Benzyl 2-O-acetyl-3-O-methyl-α-L-idopyranosyluronate)-(1→4)-2-O-benzyl-3,6-di-O-methyl-α-D-glucopyranoside 50

Compound 49 was converted to the title compound according the same procedures described for the preparation of compound 16.

TLC: Rf=0.37, dichloromethane/methanol: 9/1, v/v

Synthesis of EFGH-tetrasaccharide 52 (Scheme 4)

Compound 51

Compound 25 and compound 50 were coupled to give the title compound according the same procedures described for the preparation of compound 26.

TLC: Rf=0.52, dichloromethane/methanol: 98/2, v/v

Methyl-O-(Benzyl 2,4-di-O-dimethyl-β-D-glucopyranosyluronate)-(1→4)-O-(3-O-acetyl-2-O-benzyl-6-O-methyl-α-D-glucopyranosyl-(1→4)-O-(benzyl 2-O-acetyl-3-O-methyl-α-L-idopyranosyluronate)-(1→4)-2-O-benzyl-3,6-di-O-methyl-α-D-glucopyranoside 52

Compound 51 was converted to the title compound according the same procedures described for the preparation of compound 27.

TLC: Rf=0.26, dichloromethane/methanol: 98/2, v/v

Synthesis of DEFGH-pentasaccharide 56 (Scheme 4+5) (Example III)

Compound 53

Compound 28 and compound 52 were coupled to give the title compound according the same procedures described for the preparation of compound 29.

TLC: Rf=0.63, dichloromethane/methanol: 98/2, v/v

Compound 54

Compound 53 was converted to the title compound according the same procedures described for the preparation of compound 30.

TLC: Rf=0.51, dichloromethane/methanol: 8/2, v/v

Compound 55

Compound 54 was converted to the title compound according the same procedures described for the preparation of compound 31.

TLC: Rf=0.32, ethyl acetate/pyridine/acetic acid/water: 10/7/1.6/4, v/v

Methyl O-(2,3,4-tri-O-methyl-6-O-sulfo-α-D-glucopyranosyl)-(1→4)-O-(2,3-di-O-methyl-β-D-glucopyranosyluronic acid)-(1→4)-O-(6-O-methyl-2,3-di-O-sulfo-α-D-glucopyranosyl)-(1→4)-O-(3-O-methyl-2-O-sulfo-α-L-idopyranosyluronic acid)-(1→4)-3,6-di-O-methyl-2-O-sulfo-α-D-glucopyranoside, Heptasodium Salt 56

Compound 55 was converted to the title compound according the same procedures described for the preparation of compound 32.

$[\alpha]^{20}_D$=+50.2 (c=1.05, H$_2$O)

Anomeric protons chemical shifts: 5.32, 5.29 and 4.89 ppm.

Preparation of Example IV (Compound 80)

Synthesis of EF-disaccharide 66 (Scheme 6)

Compound 58

Et$_3$N (43 ml, 0.3 mmol), 4-dimethylaminopyridine (156 mg, 1.3 mmol) and Ac$_2$O (23 ml, 0.29 mol) were added to a solution of 57 (36.2 g, 0.128 mol) (Petroni et al. Aust. J. Chem. 1988, 41, 91–102) in CH$_2$Cl$_2$ (360 ml). After 30 min. the mixture was successively washed with 5% aq KHSO$_4$, H$_2$O, saturated aqueous NaHCO$_3$, H$_2$O and dried (Na$_2$SO$_4$). The evaporation gave crude 58: TLC, R$_f$0.41, 3:1 cyclohexane/EtOAc.

Compound 59

Ethanolamine (4.9 ml, 80 mmol)) was added, at +4° C., to a solution of crude 58 (11.8 g, 32 mmol) in THF (220 ml). After 16 h at +4° C., trichloroacetonitrile (65 ml, 644 mmol) and K$_2$CO$_3$ (8.3 g, 64.4 mmol) were added under argon to the above mixture. After 16 h at room temperature, the solution was filtered and concentrated. Column chromatography (4:1 cyclohexane/EtOAc) afforded 59 in 79% yield: TLC R$_f$0.49, 1:1 cyclohexane/EtOAc.

Compound 61

A solution of trimethylsilyl triflate (0.04 M in CH$_2$Cl$_2$; 96 ml, 3.8 mmol) was added dropwise, under argon, to a cooled (−20° C.) solution of the donor imidate 59 (11.93 g, 25 mmol) and acceptor 60 (9.2 g, 19.8 mmol) (P. J. Garegg, H. Hultberg Carbohydr. Res. 1961, 93, C10) in CH$_2$Cl$_2$ (190 ml) containing 4 Å powdered molecular sieves. After 30 minutes solid NaHCO$_3$ was introduced, and the solution was filtered, washed with water, dried (Na$_2$SO$_4$) and concentrated. The residue crystallized in Et$_2$O gave 61 (82% yield). mp: 138° C.

Compound 62

Sodium (373 mg, 0.65 mmol) was added to a solution of compound 61 (1 g, 1.3 mmol) in 2:1 methanol/CH$_2$Cl$_2$ (ml). The mixture was stirred for 1 h at room temperature, and then neutralized with Dowex 50 H$^+$ resin, filtered and concentrated to afford crude 62.

Compound 63

NaH (40.5 mg, 1.68 mmol) was added portionwise to a cooled (0° C.) solution of crude 62 (950 mg,) and MeI (0.1 ml, 1.55 mmol) in DMF (9 ml). After 2 h at room temperature, MeOH was introduced, and the mixture was poured into H$_2$O. The product was extracted with EtOAc, washed with H$_2$O, dried (Na$_2$SO$_4$) and concentrated. Column chromatography (3:1 cyclohexane/EtOAc) of the residue gave pure 63 (86% yield from 62): mp 137° C. (Et$_2$O).

Compound 64

A solution of 63 (1.16 g, 1.56 mmol) in 1:3 H$_2$O/MeOH (40 ml) was heated at 80° C. in presence of p-toluenesulfonic acid (230 mg, 1.56 mmol). After 3 h, the mixture was neutralized with NaHCO$_3$ and concentrated. Column chromatography (3:1 cyclohexane/acetone) of the residue gave 64 (89% yield): TLC R$_f$0.28, 2:1 cyclohexane/acetone.

Methyl O-(benzyl 2,3-di-O-methyl-β-D-glucopyranosyluronate)-(1→4)-2,3,6-tri-O-benzyl-α-D-glucopyranoside 66

To a solution of 64 (860 mg, 1.3 mmol) in CH$_2$Cl$_2$ (4 ml) were added 2,2,6,6-tetramethyl-1-piperidinyl oxy (2.3 mg), saturated aqueous NaHCO$_3$ (2.5 ml), KBr (13.5 mg) and tetrabutylammonium chloride (18 mg). To the above cooled (0° C.) solution was added the mixture of solutions saturated aqueous NaCl (2.8 ml), saturated aqueous NaHCO$_3$ (1.4 ml)

and NaOCl (1.3 M, 3.2 ml). After 1 h, the mixture was extracted with $CH_2Cl_2$, washed with $H_2O$, dried ($Na_2SO_4$) and concentrated to give the crude acid 65.

The crude above acid in DMF was treated with BnBr (1.6 ml, 13 mmol) and $KHCO_3$ (650 mg, 6.5 mmmol). After 16 h, the product was extracted with EtOAc, washed with $H_2O$, dried ($Na_2SO_4$) and concentrated to give 66 in 77% yield.

Synthesis of DEF-trisaccharide 70 (Scheme 7)

Compound 67

A solution of trimethylsilyl triflate (0.04 M in $CH_2Cl_2$; 1.88 ml, 0.075 mmol) was added dropwise, under argon, to a cooled (−20° C.) solution of 6-O-acetyl-2,3,4-tri-O-methyl-D-glucopyranose trichloroacetimidate 28 (290 mg, 0.711 mmol) (P. Westerduin et al. Bioorg Med. Chem. 1994, 2, 1267–83) and acceptor 66 (300 mg, 0.4 mmol) in $CH_2Cl_2$ (20 ml) containing 4 Å powdered molecular sieves. After 30 minutes solid $NaHCO_3$ was introduced, and the solution was filtered and concentrated. Column chromatography (3:1 toluene/EtOAc) of the residue gave pure 67 (56% yield): TLC $R_f$ 0.32, 3:2 toluene/EtOAc.

Compound 68

To a solution of 67 (201 mg, 0.20 mmol) in acetic anhydride (7.6 ml) at −20° C. a mixture of concentrated sulfuric acid in acetic anhydride (1.5 ml, 0.1:1 v/v) was added. After stirring 1 h sodium acetate (780 mg) was added. The mixture was diluted was EtOAc, washed with $H_2O$, dried ($Na_2SO_4$) and concentrated to give, after column chromatography (1:1 toluene/EtOAc), 68 (82% yield): TLC $R_f$ 0.32, 1:1 toluene/EtOAc.

Compound 69

Benzylamine (0.58 ml, 5.26 mmol) was added to a solution of the 68 (125.4 mg) in THF (5 ml). After 7 h at room temperature the solution was washed with 1 M aqueous HCl, $H_2O$, dried, and concentrated. Column chromatography (3:2 toluene/EtOAc) afforded pure 69 (75% yield): TLC $R_f$ 0.33, 2:3 toluene/EtOAc.

O-(6-O-acetyl-2,3,4-tri-O-methyl-α-D-glucopyranosyl)-(1→4)-O-(benzyl 2,3-di-O-methyl-β-D-glucopyranosyluronate)-(1→4)-3,6-di-O-acetyl-2-O-benzyl-D-glucopyranosyl Trichloroacetimidate 70

Trichloroacetonitrile (69 μl, 0.675 mmol), and cesium carbonate (66 mg, 0.202 mmol), were added under argon to a solution of 69 (89.2 mg, 0112 mmol) in $CH_2Cl_2$ (2 ml). After 2 h the solution was filtered and concentrated. Column chromatography of the residue (1:1 toluene/EtOAc) afforded 70 (88% yield): TLC $R_f$ 0.44, 1:1 toluene/EtOAc.

Synthesis of GH-disaccharide 76 (Scheme 2)

Compound 72

Sodium methoxide (570 mg, 106 mmol) was added to a solution of compound 71 (2.5 g, 3.53 mol) (M. Petitou er al. J. Med. Chem. 1997, 40, 1600–1607) in 1:1 methanol/$CH_2Cl_2$ (35 ml). After 2 h Dowex 50 H$^+$ resin was introduced until neutralisation and filtered. After concentration, column chromatography (2:1 cyclohexane/EtOAc) of the residue gave 72 (100% yield): TLC $R_f$ 0.32, 2:1 cyclohexane/EtOAc.

Compound 73

MeI (0.41 ml, 6.61 mmol) was added, at 0° C., to a solution of 72 (2 g, 3.3 mmol), and NaH (0.12 g, 5 mmol), in THF (20 ml). After 2 h MeOH was introduced dropwise, and after 15 min the product was extracted with $CH_2Cl_2$. The solution was washed with $H_2O$, dried ($Na_2SO_4$), and concentrated. Column chromatography (5:1 cyclohexane/EtOAc) gave pure 73 (89% yield): $[\alpha]_D$ +12° (c 1; $CH_2Cl_2$).

Compound 74

Aqueous $CF_3COOH$ (70%, 3.14 ml) was added to a solution of 73 (1.76 g, 2.84 mmol) in $CH_2Cl_2$ (16 ml). After 50 min at room temperature the solution was diluted with $CH_2Cl_2$, washed with cold saturated aqueous $NaHCO_3$, $H_2O$, and dried ($Na_2SO_4$). After concentration, column chromatography (11:2 $CH_2Cl_2$/acetone) of the residue yielded 74 in 88% yield): $[\alpha]_D$ +10° (c 1; $CH_2Cl_2$).

Methyl O-(benzyl 2,3-di-O-methyl-α-L-idopyranosyluronate)-(1→4)-2,6-di-O-benzyl-3-O-methyl-α-D-glucopyranoside 76

To a solution of 74 (1.39 g, 2.4 mmol) in THF (8 ml) were added 2,2,6,6-tetramethyl-1-piperidinyl oxy (37.4 mg), saturated aqueous $NaHCO_3$ (14.4 ml), KBr (120 mg) and tetrabutylammonium chloride (180 mg). To the above cooled (0° C.) solution was added the mixture of solutions saturated aqueous NaCl (2.8 ml), saturated aqueous $NaHCO_3$ (1.4 ml) and NaOCl (1.3 M, 3.2 ml). After 1 h, the mixture was extracted with $CH_2Cl_2$, washed with $H_2O$, dried ($Na_2SO_4$) and concentrated to give the crude acid 75.

The above crude acid 75 in DMF (31 ml) was treated with BnBr (2.84 ml, 23.9 mmol) and $KHCO_3$ (1.2 g, 12 mmmol). After 16 h, the product was extracted with EtOAc, washed with $H_2O$, dried ($Na_2SO_4$). After concentration, column chromatography (3:2 cyclohexane/EtOAc) of the residue gave 76 (78% yield from 74): $[\alpha]_D$ +7.3° (c 1.1; $CH_2Cl_2$).

Synthesis of DEFGH-pentasaccharide 80 (Scheme 8) (Example IV)

Compound 77

Trimethylsilyl triflate (170 μL, 0.0068 mmol) was added under argon to a stirred, cooled (−20° C.) solution of imidate 70 (91 mg, 0.097 mmol), and 76 (66.2 mg, 0.097 mmol), in $CH_2Cl_2$ (2 ml) containing 4 Å molecular sieves. After 30 min, solid $NaHCO_3$ (0.1 g) was introduced, and stirring was prolonged overnight. The solution was filtered, washed with $H_2O$, dried, and concentrated. Column chromatography (2:1 cyclohexane/acetone) provided the pentasaccharide 77 (71.6% yield): TLC $R_f$ 0.4, 2:1 cyclohexane/acetone.

Methyl O-(2,3,4-tri-O-methyl-6-O-sulfo-α-D-glucopyranosyl)-(1→4)-O-(2,3-di-O-methyl-β-D-glucopyranosyluronic acid)-(1→4)-O-(2,3-tri-O-sulfo-α-D-glucopyranosyl)-(1→4)-O-(2,3-di-O-methyl-α-L-idopyranosyluronic acid)-(1→4)-3-O-methyl-2,6-di-O-sulfo-α-D-glucopyranoside, Octasodium Salt 80

A solution of 77 (50 mg, 0.032 mmol) in DMF (5 ml) was stirred during 16 h under a weak stream of $H_2$ in the presence of 10% Pd/C catalyst (50 mg). After filtration, the solution was concentrated to give 78.

Aqueous NaOH (5 M, 0.46 ml) was added to a solution of the above crude compound in MeOH (26 ml). After 5 h Dowex 50 H$^+$ was introduced until neutral pH. The solution was concentrated, and the residue was layered on top of a Sephadex G 25 column eluted with $H_2O$. Concentration of the pooled fractions gave crude 79.

$Et_3N/SO_3$ complex (174 mg, 0.96 mmol) was added to a solution of the above compound in DMF (6 ml), and the solution was heated at 55° C. for 20 h. $NaHCO_3$ (0.33 mg dissolved in $H_2O$) was then introduced, and the solution was layered on top of a sephadex G 25 column (1.6×100 cm) equilibrated in 0.2 M NaCl. The fractions were pooled, concentrated, and desalted on the same gel filtration column, equilibrated in $H_2O$. Lyophilisation then gave pentasaccharide 80 (95% yield from 77): $[\alpha]_D$ +49° (c 1; $H_2O$).

Example V

The biological activity of the compounds of the present invention can be determined in the anti-factor Xa assay.

Activated Factor X (Xa) is a factor in the coagulation cascade. The anti-Xa activity of compounds of the present invention was assessed by measuring spectrophotometrically the rate of hydrolysis of the chromogenic substrate s-2222 exerted by Xa. This assay for anti-Xa activity in a buffer system was used to assess the $IC_{50}$-value of the test compound.

Reference compound: benzamidine
Test medium: Tromethamine-NaCl-polyethylene glycol 6000 (TNP) buffer
Vehicle: TNP buffer.
 Solubilisation can be assisted with dimethylsulphoxide, methanol, ethanol, acetonitrile or tert.-butyl alcohol which are without adverse effects in concentrations up to 1% (for DMSO) and 2.5% (for the other solvents) in the final reaction mixture.
Technique Reagents*
* All ingredients used are of a analytical grade. For aqueous solutions ultrapure water (Milli-Q quality) is used.
 1. Tromethamine-NaCl (TN) buffer
 Composition of the buffer:

| Tromethamine (Tris) | 6.057 g (50 mmol) |
|---|---|
| NaCl | 5.844 g (100 mmol) |
| Water to | 1 l |

The pH of the solution is adjusted to 7.4 at 37° C. with HCl (10 mmol.$l^{-1}$).
 2. TNP buffer
 Polyethylene glycol 6000 is dissolved in TN buffer to give a concentration of 3 g.$l^{-1}$.
 3. S-2222 solution
 One vial S-2222 (15 mg; Kabi Diagnostica, Sweden) is dissolved in 10 ml water to give a concentration of 1.5 mg.$ml^{-1}$ (2 mmol.$l^{-1}$).
 4. Xa solution
 Bovine Factor Xa Human (71 nKat.$vial^{-1}$; Kabi Diagnostica) is dissolved in 10 ml TNP buffer and then further diluted with 30 ml TNP buffer to give a concentration of 1.77 nKat.$ml^{-1}$. The dilution has to be freshly prepared.

Preparation of Test and Reference Compound Solutions

The test and reference compounds are dissolved in Milli-Q water to give stock concentrations of $10^{-2}$ mol.$l^{-1}$. Each concentration is stepwise diluted with the vehicle to give concentrations of $10^{-3}$, $10^{-4}$ and $10^{-5}$ mol.$l^{-1}$. The dilutions, including the stock solution, are used in the assay (final concentrations in the reaction mixture: $3 \cdot 10^{-3}$; $10^{-3}$; $3 \cdot 10^{-4}$; $10^{-4}$; $3 \cdot 10^{-5}$; $10^{-5}$; $3 \cdot 10^{-6}$ and $10^{-6}$ mol.$l^{-1}$, respectively).

Procedure

At room temperature 0.075 ml and 0.025 ml test compound or reference compound solutions or vehicle are alternately pipetted into the wells of a microtiter plate and these solutions are diluted with 0.115 ml and 0.0165 ml TNP buffer, respectively. An aliquot of 0.030 ml S-2222 solution is added to each well and the plate is pre-heated and pre-incubated with shaking in an incubator (Amersham) for 10 min. at 37° C. Following pre-incubation the hydrolysis of S-2222 is started by addition of 0.030 ml thrombin solution to each well. The plate is incubated (with shaking for 30 s) at 37° C. Starting after 1 min of incubation, the absorbance of each sample at 405 nm is measured every 2 min for a period of 90 min. using a kinetic microtiter plate reader (Twinreader plus, Flow Laboratories).

All data are collected in an IBM personal computer using LOTUS-MEASURE. For each compound concentration (expressed in mol.$l^{-1}$ reaction mixture) and for the blank the absorbance is plotted versus the reaction time in min.

Evaluation of responses: For each final concentration the maximum absorbance was calculated from the assay plot. The $IC_{50}$-value (final concentration, expressed in $\mu$mol.$l^{-1}$, causing 50% inhibition of the maximum absorbance of the blank) was calculated using the logit transformation analysis according to Hafner et al. (Arzneim.-Forsch./Drug Res. 1977; 27(II): 1871–3).

| Anti-factor Xa activity | |
|---|---|
| Compound (example) | $IC_{50}$ ($\mu$g · $l^{-1}$) |
| 32 (1) | 22 |
| 38 (2) | 12 |
| 56 (3) | 12 |
| 80 (4) | <2 |

Abbreviations
(Ph=phenyl; Me=methyl; Ac=acetyl; Im=trichloroacetimidyl; Bn=benzyl; Bz=benzoyl; Mbn=4-methoxybenzyl; Lev=levulinoyl)

Scheme 1

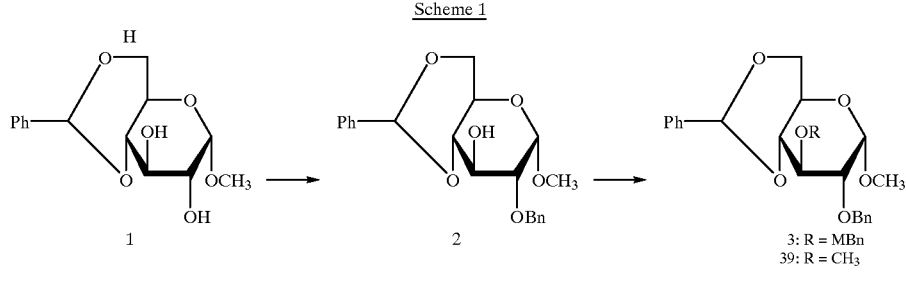

1

2

3: R = MBn
39: R = CH$_3$

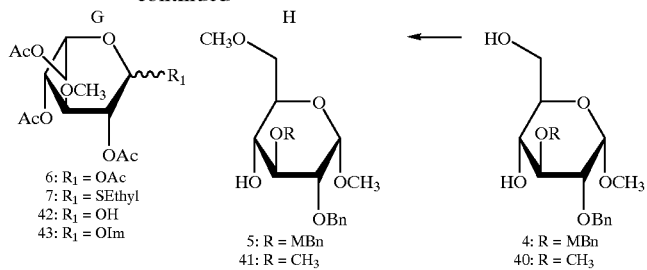

6: R₁ = OAc
7: R₁ = SEthyl
42: R₁ = OH
43: R₁ = OIm

5: R = MBn
41: R = CH₃

4: R = MBn
40: R = CH₃

| 7, 43

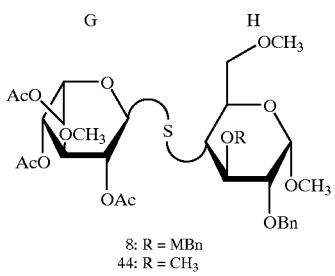

8: R = MBn
44: R = CH₃

Scheme 2

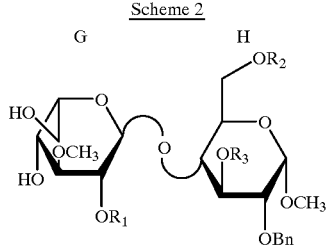

9: R₁ = H, R₂ = CH₃, R₃ = MBn
14: R₁ = R₂ = R₃ = CH₃
18: R₁ = R₂ = CH₃, R₃ = Bn
45: R₁ = H, R₂ = R₃ = CH₃
48: R₁ = Ac, R₂ = R₃ = CH₃
74: R₁ = R₃ = CH₃, R₂ = Bn

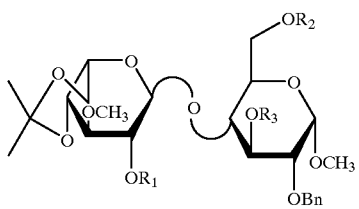

10: R₁ = H, R₂ = CH₃, R₃ = MBn
11: R₁ = R₂ = CH₃, R₃ = MBn
12: R₁ = R₂ = CH₃, R₃ = H
13: R₁ = R₂ = R₃ = CH₃
17: R₁ = R₂ = CH₃, R₃ = Bn
46: R₁ = H, R₂ = R₃ = CH₃
47: R₁ = Ac, R₂ = R₃ = CH₃
71: R₁ = Bz, R₂ = Bn, R₃ = CH₃
72: R₁ = H, R₂ = Bn, R₃ = CH₃
73: R₁ = R₃ = CH₃, R₂ = Bn

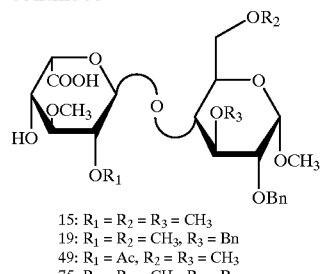

15: R₁ = R₂ = R₃ = CH₃
19: R₁ = R₂ = CH₃, R₃ = Bn
49: R₁ = Ac, R₂ = R₃ = CH₃
75: R₁ = R₃ = CH₃, R₂ = Bn

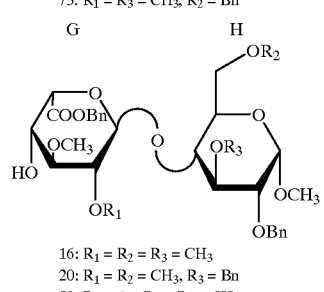

16: R₁ = R₂ = R₃ = CH₃
20: R₁ = R₂ = CH₃, R₃ = Bn
50: R₁ = Ac, R₂ = R₃ = CH₃
76: R₁ = R₃ = CH₃, R₂ = Bn

Scheme 3

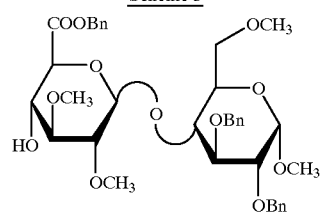

21
↓

-continued
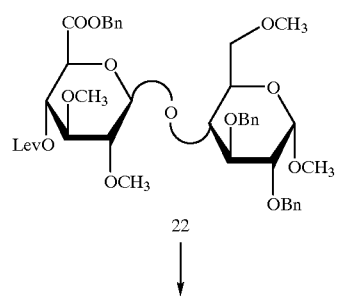
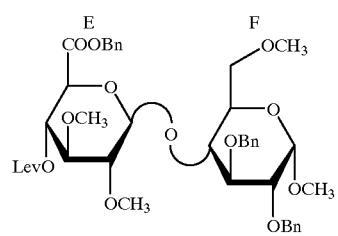
23: R = Ac
24: R = H
25: R = Im
Scheme 4
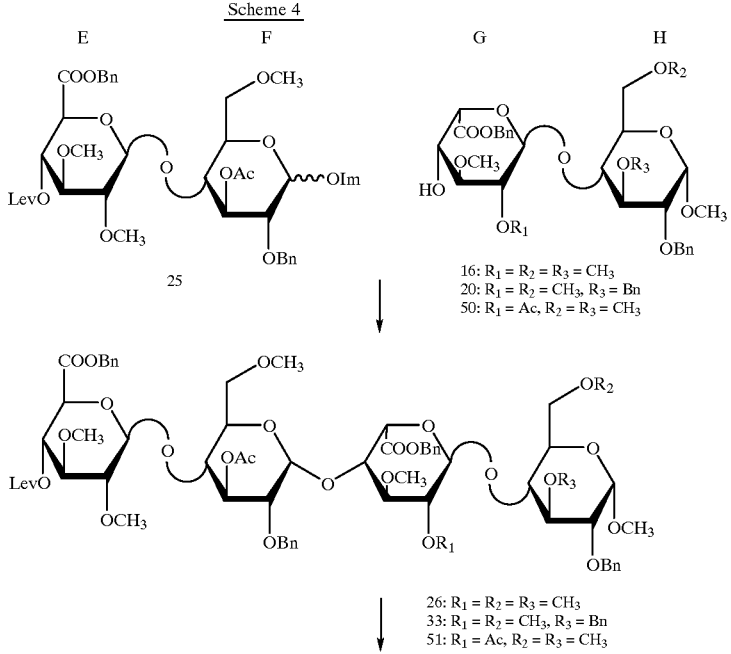
16: $R_1 = R_2 = R_3 = CH_3$
20: $R_1 = R_2 = CH_3, R_3 = Bn$
50: $R_1 = Ac, R_2 = R_3 = CH_3$
26: $R_1 = R_2 = R_3 = CH_3$
33: $R_1 = R_2 = CH_3, R_3 = Bn$
51: $R_1 = Ac, R_2 = R_3 = CH_3$
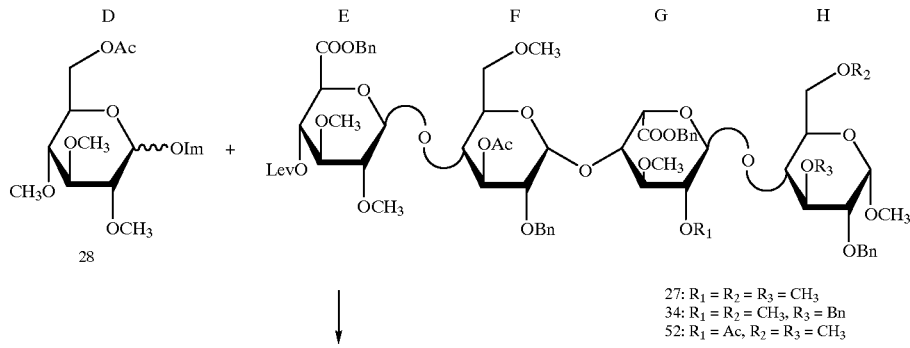
27: $R_1 = R_2 = R_3 = CH_3$
34: $R_1 = R_2 = CH_3, R_3 = Bn$
52: $R_1 = Ac, R_2 = R_3 = CH_3$ -continued
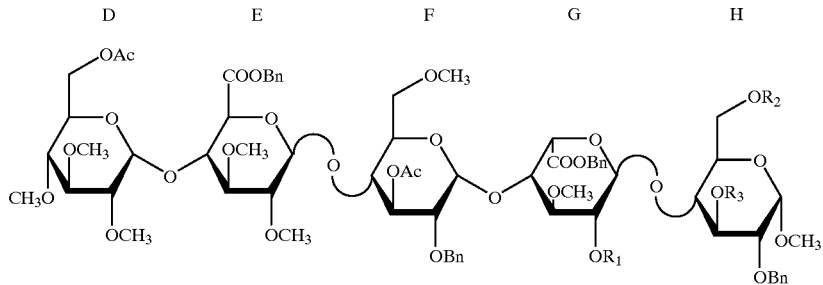
29: $R_1 = R_2 = R_3 = CH_3$
35: $R_1 = R_2 = CH_3, R_3 = Bn$
53: $R_1 = Ac, R_2 = R_3 = CH_3$
Scheme 5
29, 35, 53
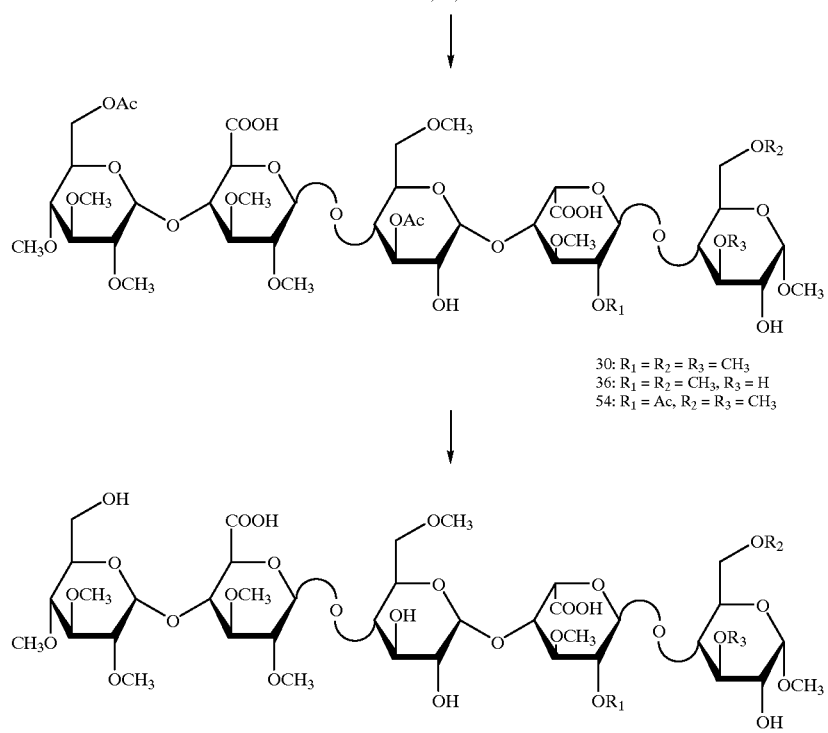
30: $R_1 = R_2 = R_3 = CH_3$
36: $R_1 = R_2 = CH_3, R_3 = H$
54: $R_1 = Ac, R_2 = R_3 = CH_3$
31: $R_1 = R_2 = R_3 = CH_3$
37: $R_1 = R_2 = CH_3, R_3 = H$
55: $R_1 = H, R_2 = R_3 = CH_3$

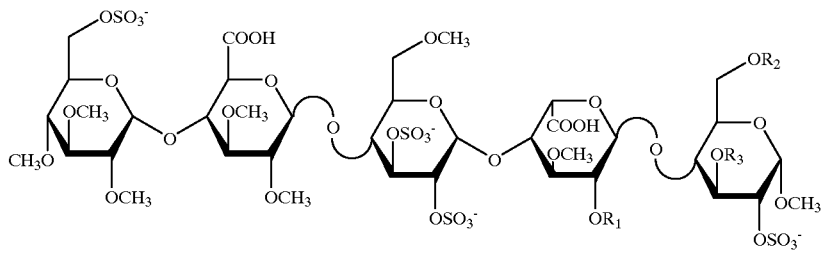
32: $R_1 = R_2 = R_3 = CH_3$ (Example I)
38: $R_1 = R_2 = CH_3, R_3 = SO_3^-$ (Example II)
56: $R_1 = SO_3^-, R_2 = R_3 = CH_3$ (Example III)
Scheme 6
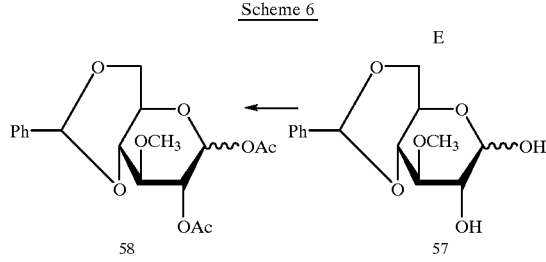
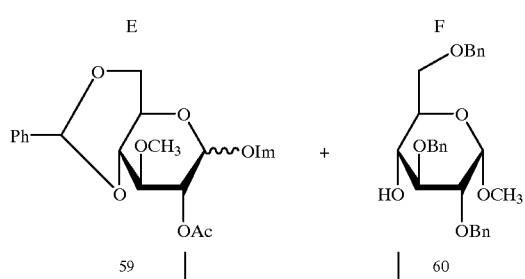
61: R = Ac
62: R = H
63: R = CH_3
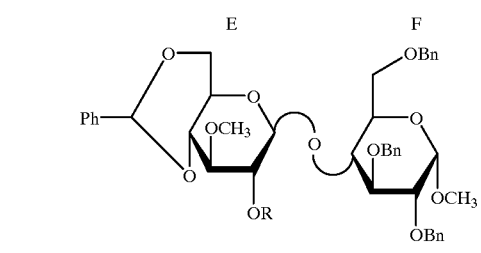
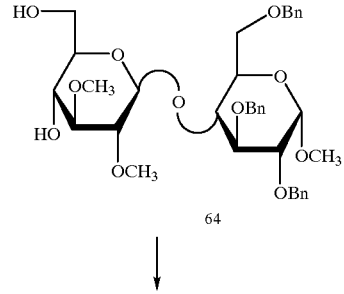
65: R = H
66: R = Bn
Scheme 7
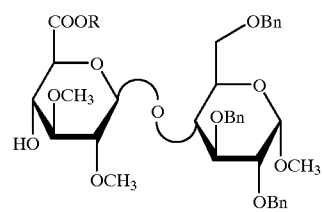
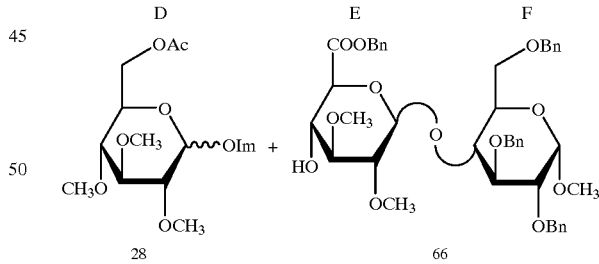

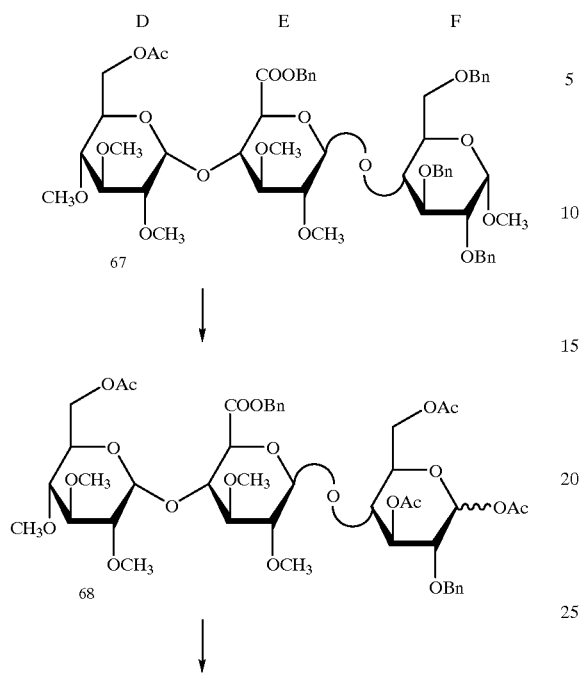
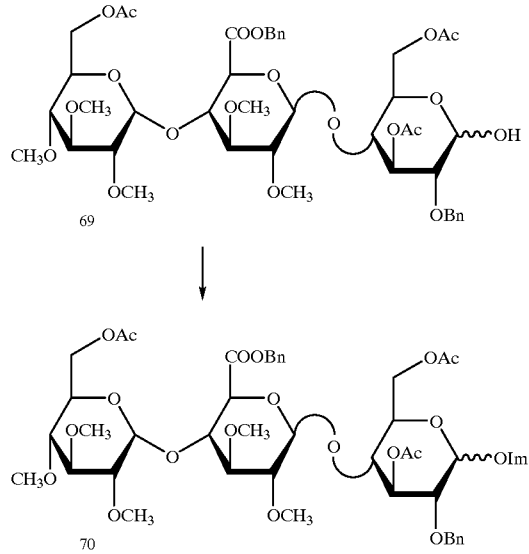
Scheme 8
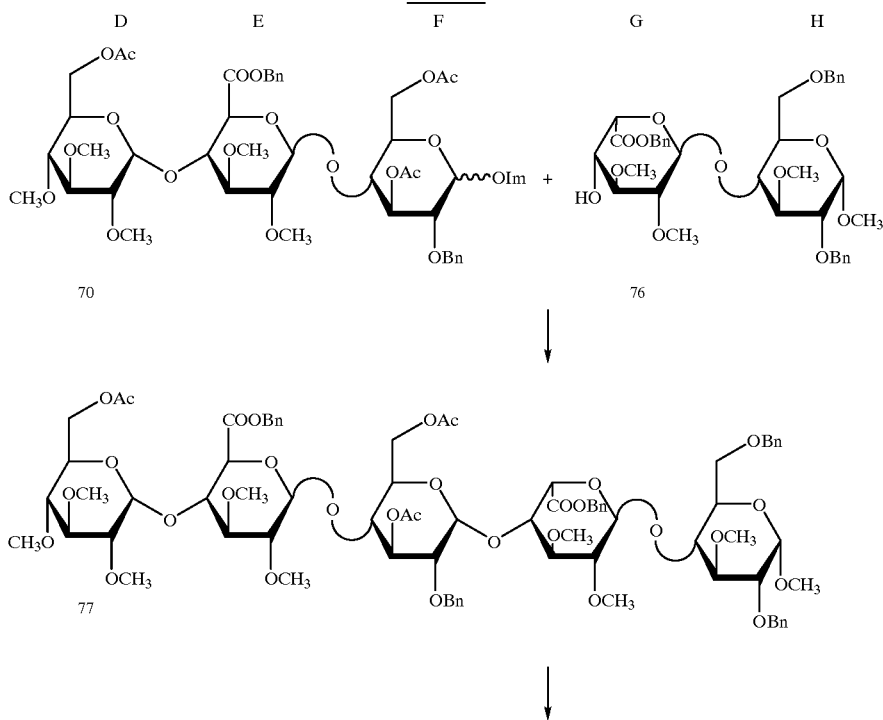

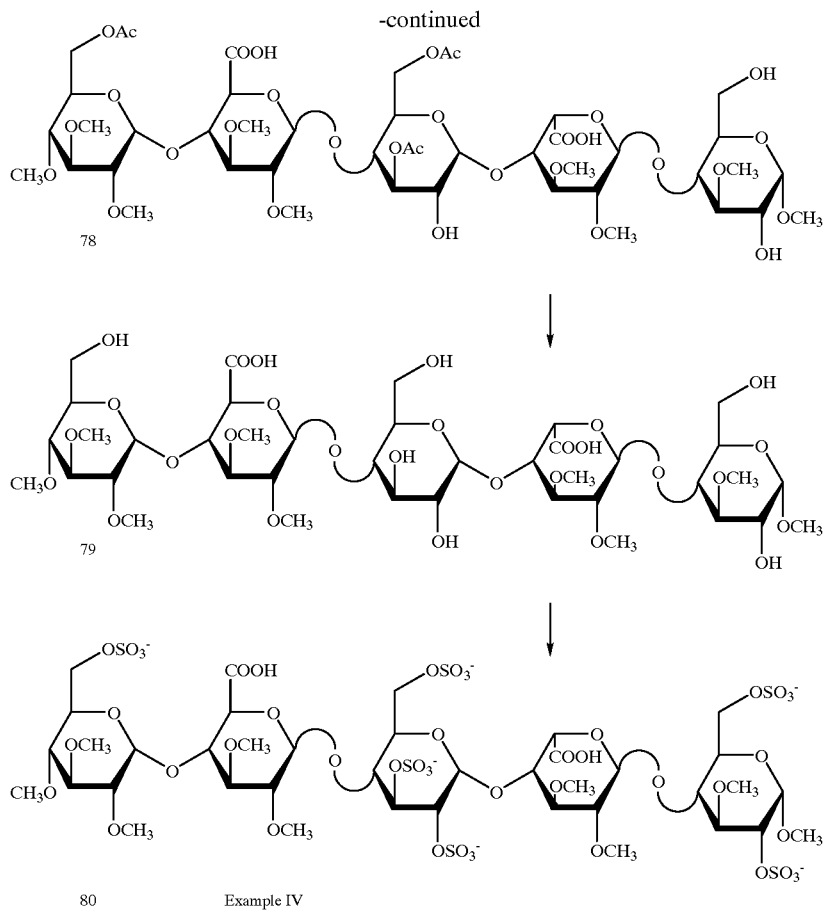

80    Example IV

What is claimed is:

1. A carbohydrate derivative having the formula I

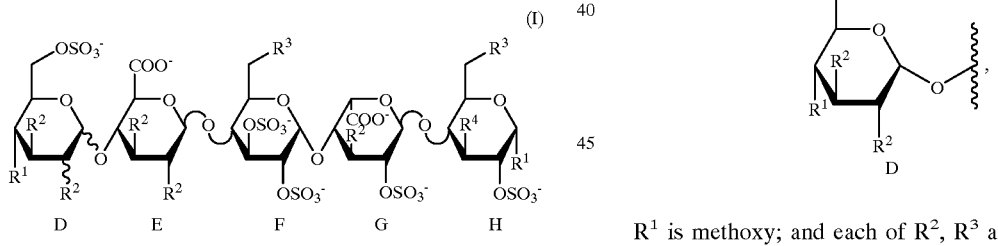

wherein $R^1$ is (1–4C)alkoxy;

each of $R^2$, $R^3$ and $R^4$ are independently (1–4C)alkoxy or $OSO_3^-$;

the total number of sulfate groups is 4, 5 or 6;

and the twisted lines represent bonds either above or below the plane of the six-membered ring to which they are attached;

or a pharmaceutically acceptable salt thereof.

2. The carbohydrate derivative of claim 1, wherein the D-unit of formula I has the structure $R^1$ is methoxy; and each of $R^2$, $R^3$ and $R^4$ are independently methoxy or $OSO_3^-$.

3. The carbohydrate derivative of claim 2, wherein $R^2$ is methoxy.

4. The carbohydrate derivative of claim 3, wherein $R^3$ is methoxy.

5. The carbohydrate derivative of claim 4, wherein $R^4$ is methoxy.

6. A pharmaceutical composition comprising the carbohydrate derivative of claim 1 and pharmaceutically suitable auxiliaries.

7. A method of treating or preventing thrombosis, or inhibiting smooth muscle cell proliferation, comprising administering to a patient in need thereof an effective amount of the carbohydrate derivative of claim 1.

8. A process for preparing a pharmaceutical composition, comprising admixing the carbohydrate derivative of claim 1 with pharmaceutically acceptable auxiliaries.

9. The carbohydrate derivative of claim 1, which has the structure:

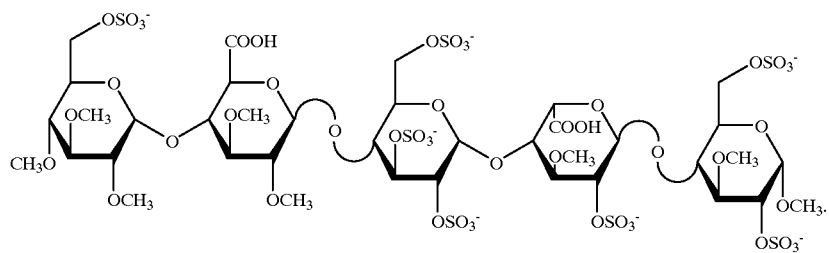
* * * * *

UNITED STATES PATENT AND TRADEMARK OFFICE
CERTIFICATE OF CORRECTION

PATENT NO.    : 6,174,863 B1                                         Page 1 of 1
DATED         : January 16, 2001
INVENTOR(S)   : Van Boeckel et al.

It is certified that error appears in the above-identified patent and that said Letters Patent is hereby corrected as shown below:

Title page,
Item [57], ABSTRACT,
Lines 20-27, please correct formula I by replacing formula I with correct formula I, as follows:
 --

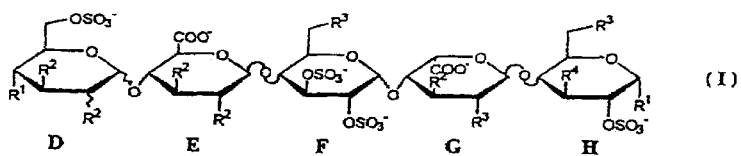

--

Column 27,
Lines 40-48, please correct formula I by replacing formula I with correct formula I, as follows:
 --

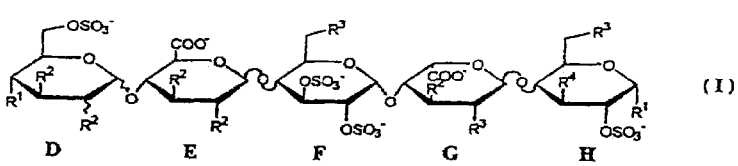

--

Signed and Sealed this

Third Day of December, 2002

JAMES E. ROGAN
*Director of the United States Patent and Trademark Office*

UNITED STATES PATENT AND TRADEMARK OFFICE
CERTIFICATE OF CORRECTION

PATENT NO. : 6,174,863 B1
DATED : January 16, 2001
INVENTOR(S) : Van Boeckel et al.

It is certified that error appears in the above-identified patent and that said Letters Patent is hereby corrected as shown below:

Column 29,
Please replace the formula as shown below.

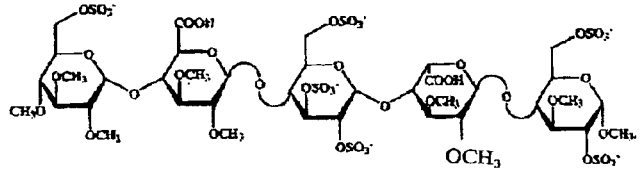

Signed and Sealed this

Eleventh Day of November, 2003

JAMES E. ROGAN
*Director of the United States Patent and Trademark Office*